US010754046B2

(12) United States Patent
Kosuge

(10) Patent No.: US 10,754,046 B2
(45) Date of Patent: Aug. 25, 2020

(54) RADIATION IMAGING SYSTEM AND RADIATION IMAGING APPARATUS

(71) Applicant: CANON KABUSHIKI KAISHA, Tokyo (JP)

(72) Inventor: Asato Kosuge, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 62 days.

(21) Appl. No.: 16/246,929

(22) Filed: Jan. 14, 2019

(65) Prior Publication Data

US 2019/0219711 A1    Jul. 18, 2019

(30) Foreign Application Priority Data

Jan. 18, 2018    (JP) .................. 2018-006686

(51) Int. Cl.
| | |
|---|---|
| A61B 6/00 | (2006.01) |
| G01T 1/20 | (2006.01) |
| G01T 1/17 | (2006.01) |
| H04N 5/32 | (2006.01) |
| G01T 1/175 | (2006.01) |
| G01T 1/208 | (2006.01) |

(52) U.S. Cl.
CPC ............. G01T 1/175 (2013.01); A61B 6/00 (2013.01); G01T 1/208 (2013.01); H04N 5/32 (2013.01)

(58) Field of Classification Search
CPC ....... A61B 6/00; A61B 6/4266; A61B 6/4283; A61B 6/54; G01N 23/04; G01T 1/175; G01T 1/208; H04N 5/32
See application file for complete search history.

(56) References Cited

U.S. PATENT DOCUMENTS

| | | | |
|---|---|---|---|
| 8,705,700 B2 | 4/2014 | Eguchi | |
| 9,787,919 B2 | 10/2017 | Kuwabara et al. | |
| 2013/0140467 A1* | 6/2013 | Kitano | G01T 1/247 250/393 |
| 2013/0279657 A1* | 10/2013 | Hiroike | A61B 6/4241 378/62 |
| 2015/0043715 A1* | 2/2015 | Kuwabara | H04N 5/369 378/62 |
| 2016/0015358 A1* | 1/2016 | Yagi | H03F 3/45475 378/62 |

(Continued)

FOREIGN PATENT DOCUMENTS

| | | |
|---|---|---|
| JP | 2014-023957 | 2/2014 |
| JP | 2014-112889 | 6/2014 |

*Primary Examiner* — Mark R Gaworecki
(74) *Attorney, Agent, or Firm* — Venable LLP

(57) ABSTRACT

A radiation imaging system is provided. The system includes radiation imaging apparatuses having an arrangement capable of detecting a start of radiation irradiation, and comprising an output unit to output a first signal representing that the apparatus itself has detected a start of irradiation and a receiving unit to receive a second signal representing that another apparatus has detected the start. In a case in which the start of irradiation is detected in a first state, the apparatus transitions to a second state for generating the image data and outputs the first signal. The apparatus in the second state generates the image data regardless of reception of the second signal. In a case in which the second signal is received in the first state, the apparatus transitions to a third state in which power consumption is lower than the first state.

14 Claims, 6 Drawing Sheets

(56) References Cited

U.S. PATENT DOCUMENTS

| | | | |
|---|---|---|---|
| 2016/0074001 A1* | 3/2016 | Matsushita | A61B 6/4405 |
| | | | 378/62 |
| 2016/0220211 A1* | 8/2016 | Yamada | A61B 6/4208 |
| 2016/0220214 A1* | 8/2016 | Yamada | A61B 6/5258 |
| 2016/0220217 A1* | 8/2016 | Uchiyama | A61B 6/4266 |
| 2016/0227130 A1* | 8/2016 | Takekoshi | H04N 5/23245 |
| 2016/0358458 A1* | 12/2016 | Kudo | A61B 6/586 |
| 2017/0311920 A1* | 11/2017 | Hiroshige | A61B 6/4283 |
| 2017/0332987 A1 | 11/2017 | Nonaka et al. | |

* cited by examiner

RADIATION IMAGING SYSTEM AND RADIATION IMAGING APPARATUS

BACKGROUND OF THE INVENTION

Field of the Invention

The present invention relates to a radiation imaging system and a radiation imaging apparatus.

Description of the Related Art

In medical imaging diagnosis or non-destructive inspection, a radiation imaging apparatus using an FPD (Flat Panel Detector) made of a semiconductor material is widely used. Each of Japanese Patent Laid-Open Nos. 2014-23957 and 2014-112889 discloses a radiation imaging apparatus that detects the start of radiation irradiation by a radiation generator and starts acquiring a radiation image. In addition, Japanese Patent Laid-Open No. 2014-112889 discloses a radiation imaging system in which a plurality of radiation imaging apparatuses are arranged in an imaging room.

SUMMARY OF THE INVENTION

Japanese Patent Laid-Open No. 2014-112889 shows that the radiation imaging apparatus that has detected the start of radiation irradiation transmits, to a console, information representing that the start of radiation irradiation is detected, and the console sends a signal to shift to a low power consumption mode to a radiation imaging apparatus other than the radiation imaging apparatus that has detected the radiation. When the radiation imaging apparatus other than the radiation imaging apparatus used for imaging shifts to the low power consumption mode, the power consumption of the entire radiation imaging system can be suppressed. However, in the radiation imaging system disclosed in Japanese Patent Laid-Open No. 2014-112889, if, for example, another radiation imaging apparatus exists near the radiation imaging apparatus scheduled to be used for imaging, the unexpected radiation imaging apparatus may erroneously detect radiation due to scattered radiation or the like. If the unexpected radiation imaging apparatus erroneously detects radiation irradiation, the radiation imaging apparatus scheduled to be used for imaging may shift to the low power consumption mode, and it may be impossible to acquire a radiation image. If a radiation image cannot be acquired, burden increases not only for a user but also for a patient.

An aspect of the present invention provides a technique of suppressing rejection while suppressing power consumption in a radiation imaging system using a plurality of radiation imaging apparatuses.

According to some embodiments, a radiation imaging system including a plurality of radiation imaging apparatuses each configured to generate radiation image data corresponding to a dose of radiation emitted by a radiation generator, each of the plurality of radiation imaging apparatuses having an arrangement capable of detecting that radiation irradiation from the radiation generator is started, and comprising an output unit configured to output a first detection signal representing that the radiation imaging apparatus itself has detected a start of radiation irradiation, and a receiving unit configured to receive a second detection signal representing that another radiation imaging apparatus has detected the start of radiation irradiation, wherein in a case in which the start of radiation irradiation is detected in a first state capable of detecting the start of radiation irradiation, each of the plurality of radiation imaging apparatuses transitions to a second state for generating the radiation image data and causes the output unit to output the first detection signal, the radiation imaging apparatus that has transitioned to the second state in the plurality of radiation imaging apparatuses generates the radiation image data regardless of reception of the second detection signal by the receiving unit, and in a case in which the receiving unit has received the second detection signal, the radiation imaging apparatus in the first state in the plurality of radiation imaging apparatuses transitions to a third state in which power consumption is lower than that in the first state, is provided.

According to some other embodiments, a radiation imaging apparatus having an arrangement capable of generating radiation image data corresponding to a dose of radiation and detecting that radiation irradiation is started, comprising an output unit configured to output a first detection signal representing that the radiation imaging apparatus itself has detected a start of radiation irradiation, and a receiving unit configured to receive a second detection signal representing that another radiation imaging apparatus has detected the start of radiation irradiation, wherein in capturing a radiation image, in a case in which the start of radiation irradiation is detected in a first state capable of detecting the start of radiation irradiation, the radiation imaging apparatus transitions to a second state for generating the radiation image data and causes the output unit to output the first detection signal, the radiation imaging apparatus that has transitioned to the second state generates the radiation image data regardless of reception of the second detection signal by the receiving unit, and in a case in which the receiving unit has received the second detection signal in the first state, the radiation imaging apparatus transitions to a third state in which power consumption is lower than that in the first state, is provided.

Further features of the present invention will become apparent from the following description of exemplary embodiments (with reference to the attached drawings).

DESCRIPTION OF THE EMBODIMENTS

Figure 1:
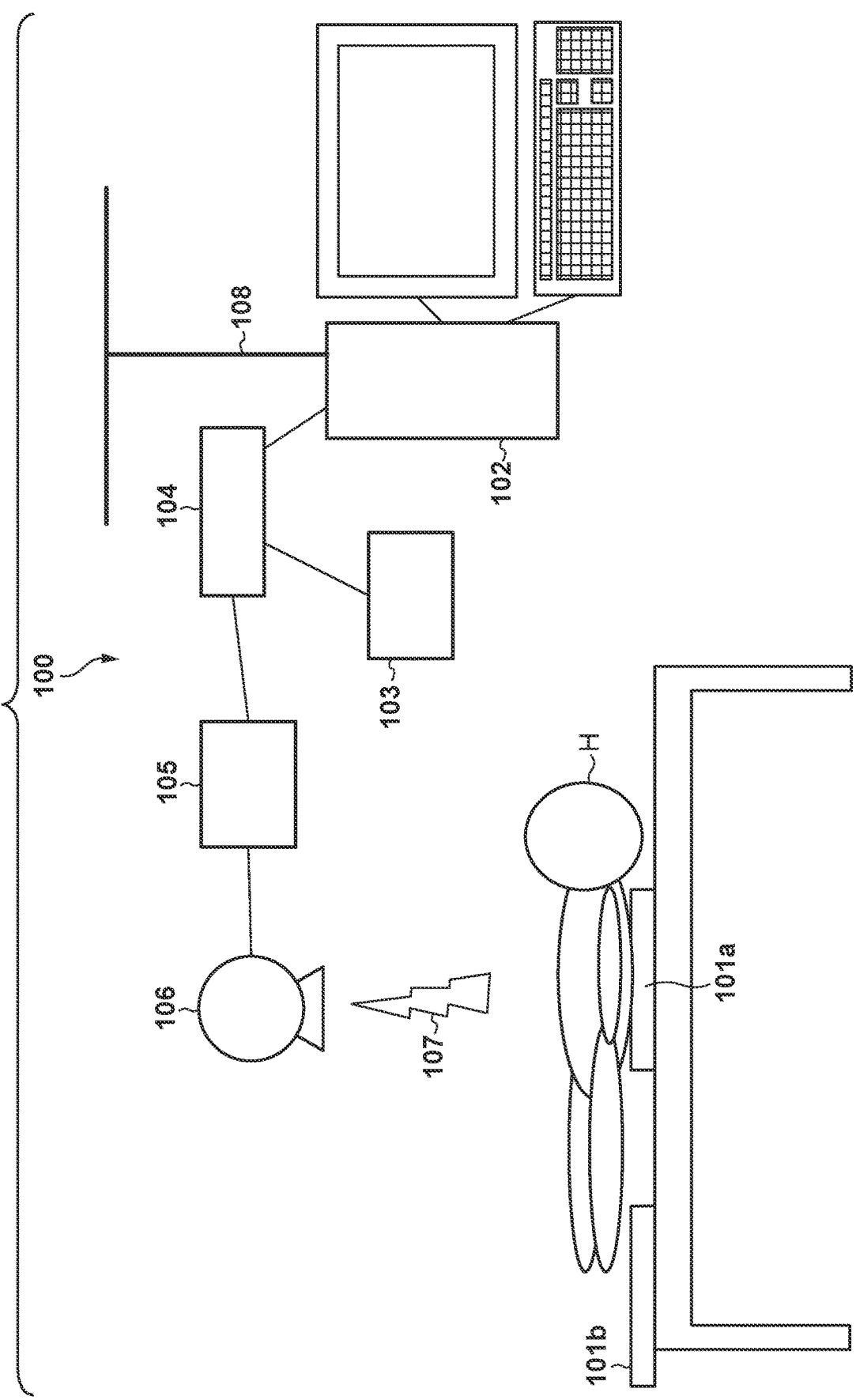
FIG. 1 is a view showing an example of the arrangement of a radiation imaging system according to an embodiment of the present invention.

A detailed embodiment of a radiation imaging system according to the present invention will now be described with reference to the accompanying drawings. In the following description and drawings, common reference numerals denote common components throughout a plurality of drawings. Hence, the common components will be described by making cross-references to the plurality of drawings, and a description of components denoted by common reference numerals will be appropriately omitted. In addition, radiation according to the present invention can include not only α-rays, β-rays, and γ-rays that are beams generated by particles (including photons) emitted by radioactive decay but also beams having equal or more energy, for example, X-rays, particle rays, and cosmic rays.

The arrangements and operations of a radiation imaging system 100 according to an embodiment of the present invention and a radiation imaging apparatus 101 used in the radiation imaging system 100 will be described with reference to FIGS. 1 to 6. FIG. 1 is a schematic view showing an example of the arrangement of the radiation imaging system 100 according to the embodiment of the present invention. The radiation imaging system 100 includes a plurality of radiation imaging apparatuses 101, a console 102, an access point 103, a HUB 104, a radiation control unit 105, and a radiation generator 106. In this specification, to indicate a specific radiation imaging apparatus of the plurality of radiation imaging apparatuses 101, a radiation imaging apparatus 101a or 101b with a suffix such as "a" or "b" is described. If a specific radiation imaging apparatus is not indicated, the radiation imaging apparatus 101 is described.

The radiation imaging apparatus 101 generates radiation image data corresponding to the dose of radiation 107 emitted by the radiation generator 106 and transmitted through a subject H. The radiation imaging apparatus 101 may be, for example, a portable type radiation imaging apparatus that can freely decide the place to install in accordance with the arrangement or imaging part of the subject H. Additionally, in this embodiment, the radiation imaging system 100 includes two radiation imaging apparatuses 101, that is, the radiation imaging apparatus 101a and the radiation imaging apparatus 101b. However, the radiation imaging system 100 may include three or more radiation imaging apparatuses 101.

The console 102 can control the entire radiation imaging system 100 by transmitting/receiving signals between the radiation generator 106 and the plurality of radiation imaging apparatuses 101. The console 102 includes an operation unit, a display unit, and the like. The console 102 transmits, for example, an imaging mode instruction input by the user via the operation unit of the console 102 to the radiation generator 106 or the radiation imaging apparatus 101. In addition, the console 102 displays, for example, a radiation image captured by the radiation imaging apparatus 101 on the display unit of the console 102.

The access point 103 is a radio wave repeater configured to connect terminals such as the plurality of radiation imaging apparatuses 101 and the console 102. The HUB 104 is a device configured to connect a plurality of network devices such as the radiation imaging apparatuses 101 and the console 102 which are connected to each other in the radiation imaging system 100.

The radiation control unit 105 includes a circuit that mediates communication and monitors the state of the radiation generator 106. For example, the radiation control unit 105 controls irradiation of the radiation 107 from the radiation generator 106 or the like in accordance with an instruction from the console 102. In addition, the radiation control unit 105 may monitor the states of the radiation imaging apparatuses 101. For example, even if an exposure instruction is received from the console 102, the radiation control unit 105 may control the radiation generator 106 not to generate the radiation 107 in a case in which the radiation imaging apparatus 101 is not ready for capturing a radiation image. To generate, for example, the radiation 107 such as X-rays, the radiation generator 106 is constituted by including a rotor and a radiation tube configured to accelerate electrons by a high voltage and collide them against an anode.

As shown in FIG. 1, the radiation imaging system 100 can be connected to an in-hospital LAN 108. The in-hospital LAN 108 is a local area network formed in a hospital.

An automatic detection mode has recently become popular, in which the radiation control unit 105 is not provided, and when the radiation generator 106 emits the radiation 107, the radiation imaging apparatus 101 automatically detects the start of radiation irradiation, accumulates image signals (charge signals), and generates a radiation image. In the arrangement shown in FIG. 1, the radiation control unit 105 is provided. However, this embodiment can also be applied to a radiation imaging system in which the radiation control unit 105 is not provided. Furthermore, this embodiment can also be applied to a radiation imaging system of an automatic detection mode, in which not only the radiation control unit 105 but also the console 102, the access point 103, and the HUB 104 are absent.

Figure 2:
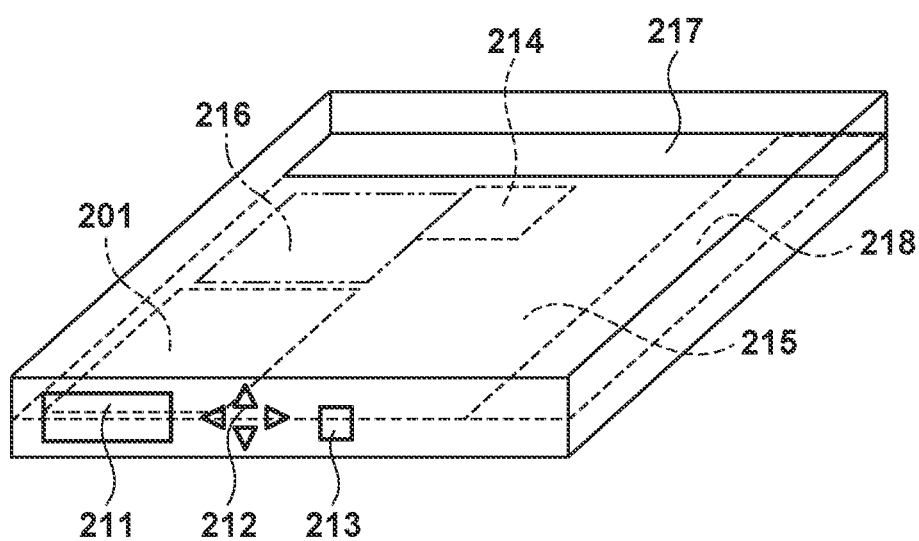
FIG. 2 is a view showing the outline of a radiation imaging apparatus used in the radiation imaging system shown in FIG. 1.
Figure 3:
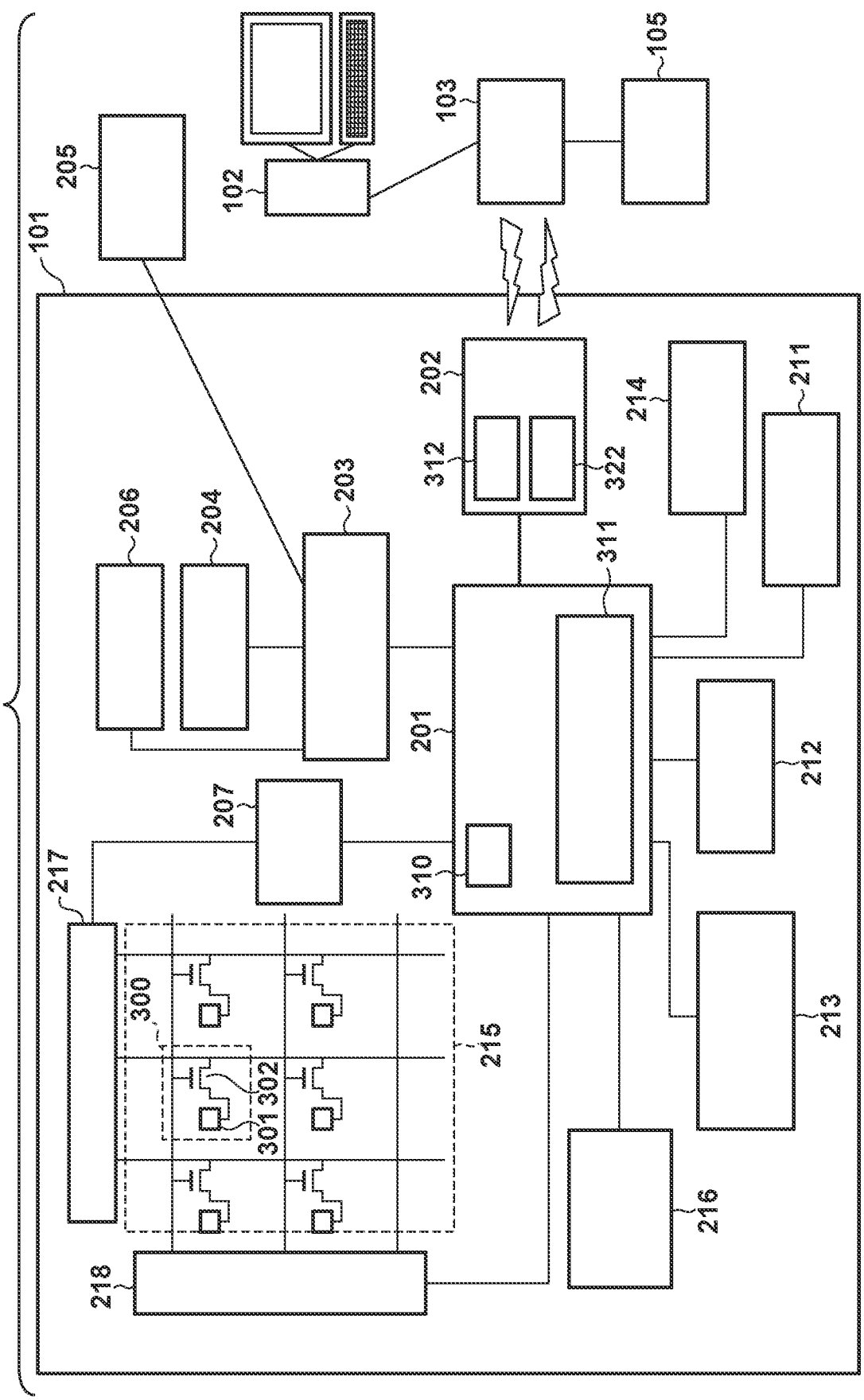
FIG. 3 is a block diagram showing an example of the arrangement of the radiation imaging apparatus shown in FIG. 2.

The radiation imaging apparatus 101 will be described next with reference to FIGS. 2 and 3. FIG. 2 shows the outline of the radiation imaging apparatus 101, and FIG. 3 shows the arrangement of the radiation imaging apparatus 101. As shown in FIGS. 2 and 3, the radiation imaging apparatus 101 includes a control unit 201, a display unit 211, an operation unit 212, a display reset unit 213, a storage unit 214, a radiation detection unit 215, an image determination unit 216, an amplifier IC 217, and a drive IC 218.

The display unit 211 has a function of displaying information stored in the storage unit 214. The display unit 211 may display, for example, information corresponding to an operation on the operation unit 212 by the user. In the arrangement shown in FIG. 2, the display unit 211 is provided on a side surface of the radiation imaging apparatus 101. However, the present invention is not limited to this. The display unit 211 can be arranged on any surface as long as it is a surface in a direction other than the incidence direction of the radiation onto the radiation imaging apparatus 101.

The operation unit 212 is an input device configured to receive a user operation and may include a button, a dial, a joystick, a touch sensor, and a touch pad. When the operation unit 212 is operated by the user, information such as imaging information or an imaging success/failure is displayed on the display unit 211. Additionally, in the arrangement shown in FIG. 2, the operation unit 212 is arranged beside the display unit 211. This is because it allows the user to perform an operation while viewing the display unit 211.

The display reset unit 213 has a function of returning the display contents displayed by the user operation on the operation unit 212 to a state before the operation. The display reset unit 213 may be provided beside the operation unit 212. The display reset unit 213 can be arranged to, for example, return, by one operation at the end of the operation, the display unit whose display is switched to the state before the switching of the display contents. When the operation unit 212 and the display reset unit 213 are arranged side by side, the user can intuitively operate them. If the reset function is included in the operation contents of the operation unit 212 to share the function of the display reset unit 213, the independent button as shown in FIG. 2 need not be provided. In addition, when the display unit 211 is a touch sensor, for example, the display unit 211 may have the same function as the display reset unit 213 to reset display by a touch.

The storage unit 214 stores radiation image data generated by the radiation imaging apparatus 101 and various kinds of information. The various kinds of information can be, for example, a technician ID assigned to each user (technician) who performs imaging, a patient ID assigned to each subject (patient), an imaging time, an imaging dose [mAs], an imaging part, the number of captured images of the day, a result of determining success/failure of imaging by the image determination unit 216, and the like. The pieces of information can be associated with each image data. In addition, these pieces of information may be output to the display unit 211 at an arbitrary timing. The storage unit 214 is a device capable of readout/write, and corresponds to, for example, a flash memory. However, the storage unit 214 is not limited to the flash memory and may be another storage device such as, for example, a hard disk.

The radiation detection unit 215 detects the radiation 107 that has passed through the subject H and entered the radiation detection unit 215 as an image signal (charge signal). In the radiation detection unit 215, pixels 300 each including a conversion element 301 configured to convert the radiation 107 that has entered into charges are arranged in an array, as shown in FIG. 3. The conversion element 301 may be an indirect-type conversion element including a scintillator, and a photoelectric conversion element configured to convert light converted from the radiation 107 by the scintillator into an image signal (charge signal) that is an electrical signal. Alternatively, the conversion element 301 may be a direct-type conversion element configured to directly convert the radiation 107 that has entered into an electrical signal. In this way, the radiation detection unit 215 detects the radiation 107 transmitted through the subject H and acquires an image signal.

The control unit 201 controls the overall operation of the radiation imaging apparatus 101. For example, the radiation imaging apparatus 101 may include a display control unit 311 configured to control the display on the display unit 211. The procedure of generating radiation image data in the radiation imaging apparatus 101 will briefly be described here. Under the control of the control unit 201, the drive IC 218 forms a drive circuit unit that gives a drive signal to the radiation detection unit 215. More specifically, when one row is selected by the drive IC 218, switch elements 302 of the pixels 300 of the row sequentially perform an ON (conductive) operation. Accordingly, image signals (charge signals) accumulated in the conversion elements 301 of the pixels 300 of the row are output to signal lines connected to the pixels 300. The amplifier IC 217 sequentially reads out the image signals output to the signal lines. Each readout image signal is transmitted to the control unit 201 via an ADC 207 shown in FIG. 3. The ADC 207 converts the image signal that is an analog signal read out by the amplifier IC 217 into an image signal as a digital signal and outputs the signal as a radiation image to the control unit 201. That is, the ADC 207 forms an A/D conversion unit configured to convert the image signal as an analog signal read out by the amplifier IC 217 into digital data. The amplifier IC 217 can be an IC that amplifies the signal sent from each pixel 300 of the radiation detection unit 215. In addition, the drive IC 218 is an IC that causes each pixel 300 of the radiation detection unit 215 to perform charge accumulation and readout operations. The control unit 201 causes the storage unit 214 to store the radiation image data output from the ADC 207. The storage unit 214 can store the radiation image data based on the image signal obtained by the radiation detection unit 215, imaging conditions at the time of imaging, and various kinds of information such as time in association with each other, as described above. The image determination unit 216 has a function of determining whether the radiation image generated by the radiation detection unit 215 satisfies predetermined criteria. The predetermined criteria include a pixel value, a dose [mAs], an artifact, body movement detection, foreign substance detection, impact detection, error reception from the radiation generator, and the like at the time of generation of the radiation image.

Furthermore, as shown in FIG. 3, the radiation imaging apparatus 101 includes a communication unit 202, a power supply control unit 203, and a power button 206. The communication unit 202 performs, for example, wireless communication with the console 102 and the radiation control unit 105 via the access point 103. The communication unit 202 may transmit a signal using broadcast communication. The communication unit 202 includes an output unit 312 configured to output a detection signal representing that the radiation imaging apparatus 101 itself has detected the start of radiation irradiation. The communication unit 202 also includes a receiving unit 322 configured to receive a detection signal representing that the other radiation imaging apparatus 101 included in the radiation imaging system 100 has detected the start of radiation irradiation. In the arrangement shown in FIG. 3, the output unit 312 and the receiving unit 322 are illustrated as separate components but may be an integrated component. Additionally, in this embodiment, the communication unit 202 communicates with the console 102 and the radiation control unit 105 by wireless communication via the access point 103 but may communicate by wired communication.

The power button 206 is a button operated by the user to start/stop power supply. The power supply control unit 203 connects a battery unit 204 or an external power supply 205 in accordance with the operation state of the power button 206. For example, in a case in which the external power supply 205 is not connected to the radiation imaging apparatus 101, when the power button 206 is operated, the power supply control unit 203 switches ON/OFF of supply of power from the battery unit 204. In addition, the power supply control unit 203 controls power supply to each component in the radiation imaging apparatus 101. When performing battery driving, the power supply control unit 203 can, for example, monitor the remaining battery level of the battery unit 204. Furthermore, the power supply control unit 203 may convert a voltage supplied from the battery unit 204 or the external power supply 205 into a predetermined voltage and supply it to the components in the radiation imaging apparatus 101.

The operations of the radiation imaging system 100 and the radiation imaging apparatus 101 according to this embodiment will be described next with reference to FIG. 4. In this embodiment, the radiation imaging system 100 performs the following operation to prevent the user from using a wrong radiation imaging apparatus 101 in the radiation imaging system 100 using the plurality of radiation imaging apparatuses 101.

First, in step S401, the console 102 outputs a transition signal to instruct all the radiation imaging apparatuses 101 arranged in the same imaging room to transition to a state (first state) in which the start of radiation irradiation can be detected. According to this, the radiation imaging apparatuses 101 transition to a state in which radiation can be detected. For example, the control unit 201 of the radiation imaging apparatus 101 controls the drive IC 218 and the amplifier IC 217 to cause the radiation detection unit 215 to output a signal and determines the start of radiation irradiation based on a change in the output signal. As described above, in this embodiment, each of the plurality of radiation imaging apparatuses 101 has an arrangement capable of detecting that the radiation irradiation from the radiation generator 106 is started.

In this embodiment, according to the transition signal from the console, each radiation imaging apparatus 101 transitions to the state for detecting the start of radiation irradiation. However, the present invention is not limited to this. For example, each radiation imaging apparatus 101 may transition to the state for detecting the start of radiation irradiation when the user operates the power button 206 or the operation unit 212 of the radiation imaging apparatus 101.

Additionally, in this embodiment, a case in which two radiation imaging apparatuses 101, that is, the radiation imaging apparatus 101a and the radiation imaging apparatus 101b are arranged in one imaging room is shown, as in FIG. 1. A description will be made assuming that the user is scheduled to perform imaging of the subject H using the radiation imaging apparatus 101a of the two radiation imaging apparatuses 101. However, the present invention is not limited to this, and three or more radiation imaging apparatuses 101 may be arranged in one imaging room.

After transmitting the transition signal and making the radiation imaging apparatuses 101 transition to the state for detecting the start of radiation irradiation, the console 102 causes the radiation generator 106 to generate the radiation 107 via the radiation control unit 105 (step S402). Upon detecting the start of radiation irradiation during standby in the state capable of detecting the start of radiation irradiation, the radiation imaging apparatus 101 transitions to an imaging state (second state) for accumulating charges generated by radiation irradiation to generate radiation image data. In addition, upon detecting the start of radiation irradiation, the radiation imaging apparatus 101 causes the output unit 312 to output, to the console 102, a detection signal representing that the start of radiation irradiation is detected. Upon receiving the detection signal representing that the start of radiation irradiation is detected, the console 102 transmits, to the radiation imaging apparatus 101 other than the radiation imaging apparatus 101 that has detected the start of radiation irradiation, a signal to make the radiation imaging apparatus 101 transition to a state (third state) in which the power consumption is lower than that in the state for detecting the start of radiation irradiation. Accordingly, the radiation imaging apparatus 101 receives, by the receiving unit 322, the detection signal representing that the other radiation imaging apparatus 101 has detected the start of radiation irradiation.

However, at this time, not only the radiation imaging apparatus 101a scheduled to be used for imaging but also the radiation imaging apparatus 101b arranged near the radiation imaging apparatus 101a may detect the start of radiation irradiation. In this case, the radiation imaging apparatus 101b outputs a detection signal representing that the start of radiation irradiation is detected to the console 102. At this time, for example, the detection signal from the radiation imaging apparatus 101b that is not scheduled to be used for imaging may arrive at the console 102 before the detection signal from the radiation imaging apparatus 101a scheduled to be used for imaging (step S403). In this case, the console 102 responds to the detection signal and issues a transition instruction to the power saving mode to the radiation imaging apparatus 101a scheduled to be used for imaging (step S405). Here, if the radiation imaging apparatus 101a transitions to the state of low power consumption, images that are originally needed are lost.

In this embodiment, consider a case in which the radiation imaging apparatus 101a detects the start of radiation irradiation and transitions to the imaging state before the console 102 transmits the transition instruction to the power saving mode (step S404). In this case, the radiation imaging apparatus 101a refuses the transition instruction to the power saving mode and regardless of the reception of the detection signal, maintains the imaging state and generates radiation image data (step S406). That is, the radiation imaging apparatus 101 that has transitioned to the imaging state in the radiation imaging apparatuses 101 maintains the imaging state and generates radiation image data even if the detection signal representing that the other radiation imaging apparatus 101 has detected the start of radiation irradiation is received by the receiving unit 322. Accordingly, when the radiation imaging apparatus 101a that has detected the start of radiation irradiation and transitioned to the imaging state maintains the imaging state, a radiation image can be acquired even in a case in which the imaging apparatus other than the radiation imaging apparatus 101a scheduled to be used for imaging detects radiation.

Figure 4:
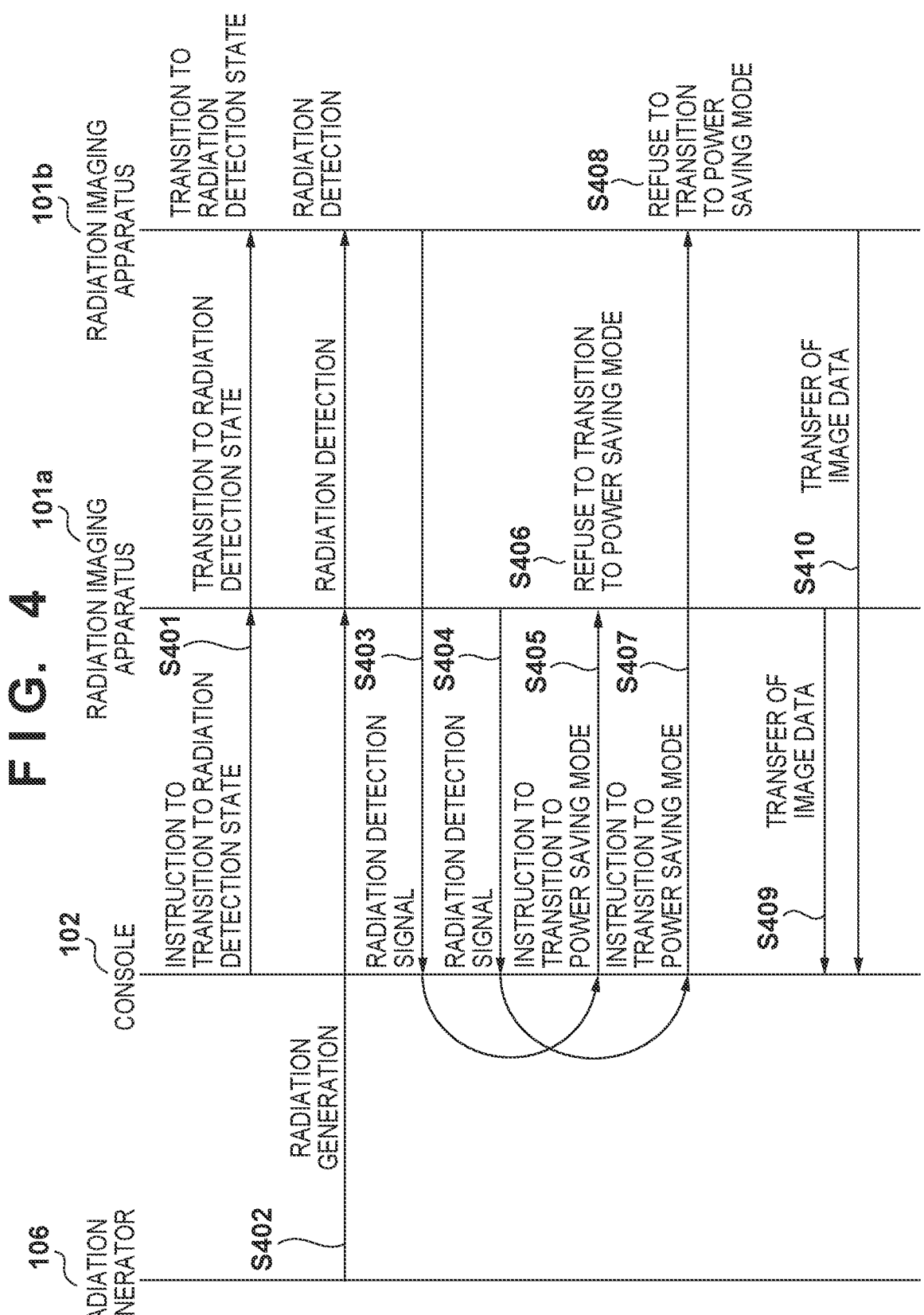
FIG. 4 is a sequence chart showing the timing of communication of the radiation imaging system shown in FIG. 1.

Referring to FIG. 4, the radiation imaging apparatus 101a also outputs a signal representing that the start of radiation irradiation is detected to the console 102 (step S404). In response to this, the console 102 outputs the transition instruction to the power saving mode to the radiation imaging apparatus 101b (step S407). However, since already transitioned to the imaging state, the radiation imaging apparatus 101b refuses the transition instruction and maintains the imaging state (step S408).

After capturing the radiation images, the radiation imaging apparatus 101a and the radiation imaging apparatus 101b in the imaging state transfer the acquired radiation image data to the console 102 (steps S409 and S410). The user confirms each radiation image displayed on the display unit of the console 102 and, for example, uses the radiation images acquired by the radiation imaging apparatus 101a for a diagnosis and the like, and discards the radiation images acquired by the radiation imaging apparatus 101b. The image determination unit 216 of the radiation imaging apparatus 101 may determine whether acquires radiation image data captures the subject H or not. For example, if the contrast ratio of the radiation image data is low, the image determination unit 216 determines that the subject H is not captured and need not transfer the radiation image data to the console 102.

Here, to more reliably perform imaging using the radiation imaging apparatus 101 scheduled to acquire radiation images, the radiation imaging apparatus 101 that has detected the start of radiation irradiation may cause the output unit 312 to output the detection signal after a predetermined time has elapsed from the detection of the start of radiation irradiation. Even in a case in which an error occurs in the detection of the start of radiation irradiation, when the timing to output the detection signal is delayed, the radiation imaging apparatus 101 scheduled to perform imaging transitions to the imaging state at a high possibility before the transition instruction to the state of low power consumption is received from the console 102. For example, the detection signal may be output after an appropriately set time, for example, 0.1 sec or 1 sec after the start of radiation detection. This time may be set in advance at the time of shipping of the radiation imaging apparatus 101, may be set by a serviceman when forming the radiation imaging system 100, or may be set by the user in each imaging. In addition, for example, the radiation imaging apparatus 101 that has detected the start of radiation irradiation may output the signal representing that the start of radiation irradiation is detected after the imaging of the radiation images ends, and the radiation image data are output.

In addition, generation of a time lag to prevent rejection is not limited to delaying the output, by the radiation imaging apparatus 101, of the detection signal representing that the start of radiation irradiation is detected. For example, consider a case in which in the radiation imaging apparatus 101 that is in the state capable of detecting the start of radiation irradiation, the other radiation imaging apparatus 101 outputs the detection signal representing that the start of radiation irradiation is detected, and the transition instruction to the state of low power consumption from the console 102 arrives. At this time, if the start of radiation irradiation is detected during the time from the arrival of the transition instruction to the elapse of a predetermined time, the radiation imaging apparatus 101 may transition to the imaging state.

In addition, of the plurality of radiation imaging apparatuses 101, the radiation imaging apparatus 101 designated by the operation of the user need not transition to the state of low power consumption even if the receiving unit 322 receives the detection signal representing that the other radiation imaging apparatus 101 has detected the start of radiation irradiation. For example, if, of the radiation imaging apparatuses 101, the radiation imaging apparatus 101 to be used for the next imaging is decided based on a condition such as a sensor size or scintillator type, the corresponding radiation imaging apparatus 101 refuses the transition to the power saving mode. The radiation imaging apparatus 101 that does not transition to the power saving mode may be set by the user via the operation unit of the console 102 or may be set by the user by operating the operation unit 212 of the radiation imaging apparatus 101.

Additionally, to reduce the power consumption of the radiation imaging apparatus 101, when the receiving unit 322 receives the detection signal representing that the other radiation imaging apparatus 101 has detected the start of radiation irradiation, the radiation imaging apparatus 101 that is in the state capable of detecting the start of radiation irradiation transitions to a state of lower power consumption. For example, if the start of radiation irradiation is not detected during the time from the output of the detection signal representing the detection of the start of radiation irradiation by the other radiation imaging apparatus 101 to the elapse of a predetermined time, the radiation imaging apparatus 101 may transition to the state of low power consumption. In addition, for example, if the start of radiation irradiation is not detected during a predetermined time after power-on by the user, the radiation imaging apparatus 101 may transition to the state of low power consumption. For example, if radiation irradiation is not detected for 10 min after power-on, the radiation imaging apparatus 101 transitions to the state of low power consumption.

The power mode of the radiation imaging apparatus 101 may include a power saving mode in which at least one of the communication intensity and the communication frequency of the communication unit 202 that outputs the detection signal representing that the start of radiation irradiation is detected is reduced, in addition to a normal power mode. In addition, the radiation imaging apparatus 101 may have a low power consumption mode to stop power to at least one component of circuit units including the amplifier IC 217, the drive IC 218, the ADC 207, the voltage source configured to supply a bias voltage to the conversion elements 301, the storage unit 214, and the like. The radiation imaging apparatus 101 may also have a power consumption mode to stop power to the display unit 211 is stopped. The low power consumption mode may include the power saving mode of the communication unit and a mode to stop power supply to the amplifier IC 217. In addition, the low power consumption mode may be a mode (sleep mode) to stop power supply to an image capturing unit including the radiation detection unit 215 including the plurality of pixels 300 and the above-described circuit units. In addition, the radiation imaging apparatus 101 may have the plurality of low power consumption modes. When transitioning to the above-described state of low power consumption, the radiation imaging apparatus 101 transitions to one of the power saving modes or low power consumption modes. The mode to transition is appropriately set. When the radiation imaging apparatus 101 has the plurality of low power consumption modes, the radiation imaging apparatus 101 and the radiation imaging system 100 convenient to use can be implemented while reducing the power consumption.

Figure 5:
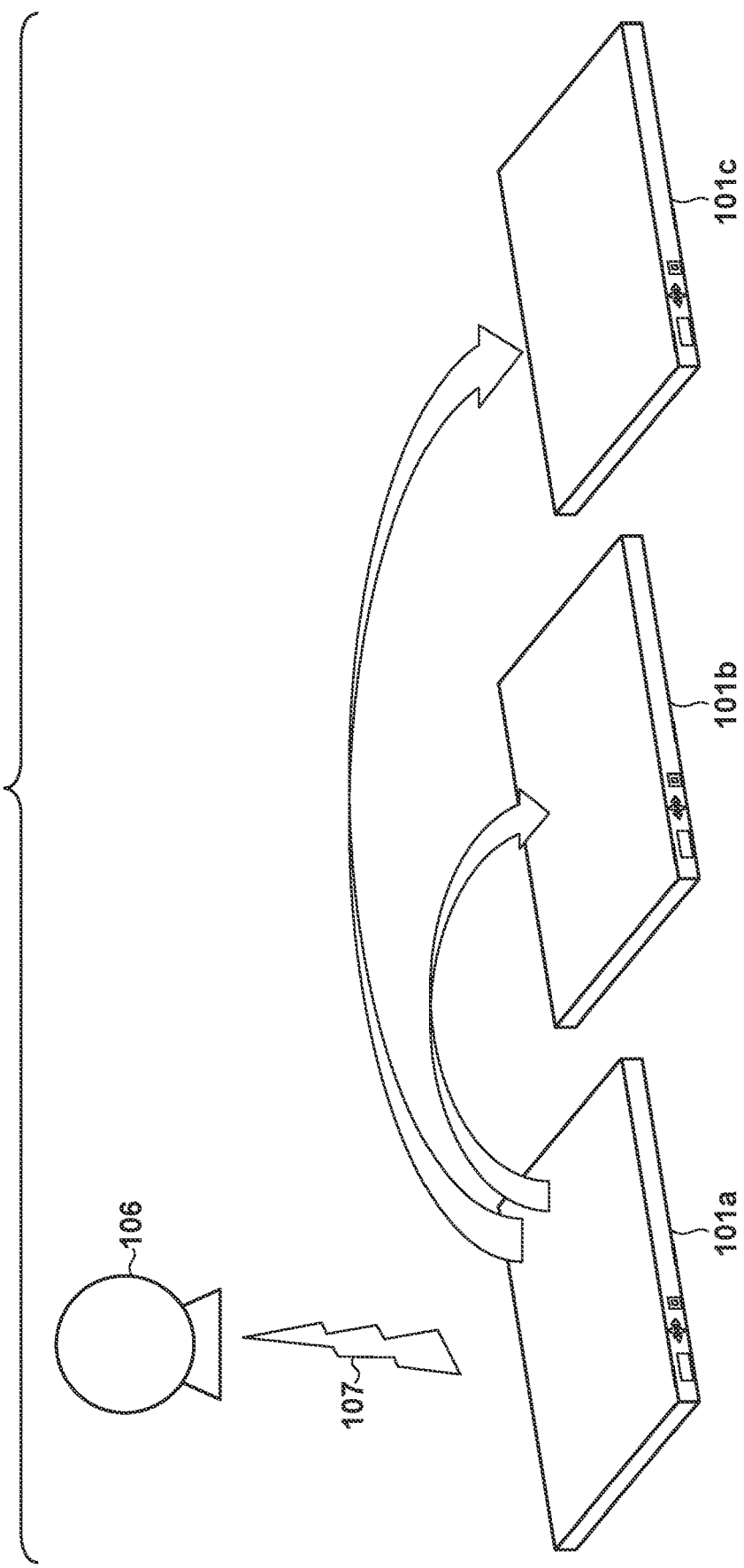
FIG. 5 is a view showing the arrangement of communication between the radiation imaging apparatuses shown in FIG. 2.

The detection signal representing the start of detection of the radiation, which is output from the output unit 312 of the radiation imaging apparatus 101, need not always be transferred to the other radiation imaging apparatus 101 via the console 102. For example, as shown in FIG. 5, the other radiation imaging apparatus 101 may receive the output detection signal representing that the start of radiation irradiation is detected without an intervention of the console 102.

The method of determining, by the radiation imaging apparatus 101, that the other radiation imaging apparatus 101 has detected the start of radiation irradiation is not limited to receiving the detection signal output from the radiation imaging apparatus 101 that has detected the start of irradiation. For example, the radiation imaging apparatus 101 may include a counter 310 configured to count time after the transition to the state capable of detecting the start of radiation irradiation until the detection of the start of radiation irradiation. The count values of the counters 310 are compared between the plurality of radiation imaging apparatuses 101, thereby identifying the radiation imaging apparatus 101 that has detected the start of radiation irradiation. More specifically, after the transition to the state capable of detecting the start of radiation irradiation, the count values of the counters 310 of the radiation imaging apparatuses 101 are compared with each other. When the count values have a difference, the radiation imaging apparatus 101 that has detected the start of radiation irradiation can be identified. For example, the count values of the counters 310 may be periodically transmitted/received between the radiation imaging apparatuses 101, and the determination may be performed by comparing the count values each time.

Figure 6:
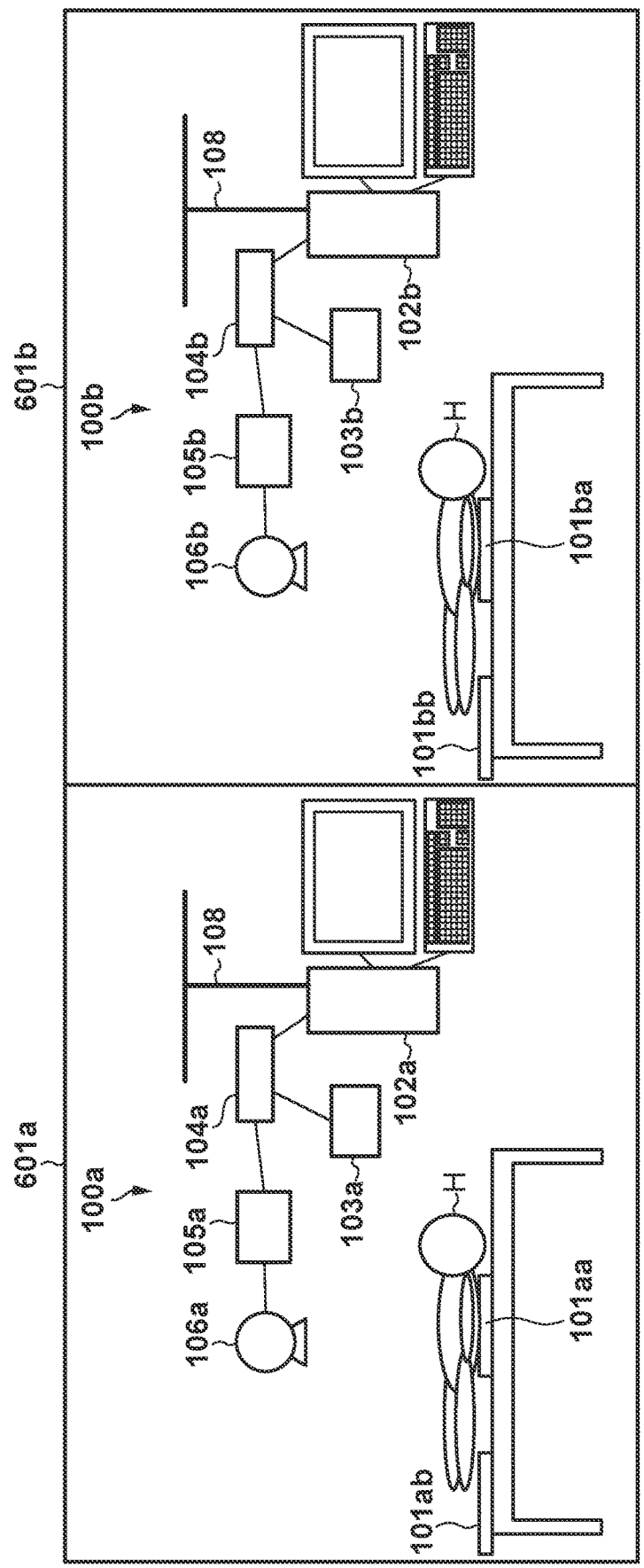
FIG. 6 is a view for explaining a case in which the radiation imaging system shown in FIG. 1 is used in a plurality of imaging rooms.

In the radiation imaging system 100, as shown in FIG. 6, radiation image capturing may be performed in each of a plurality of imaging rooms 601. That is, the radiation imaging system 100 includes a plurality of consoles 102 each of which performs communication with the radiation imaging apparatus 101. In this case, if radiation imaging apparatuses 101*ba* and 101*bb* arranged in an imaging room 601*b* comply with a signal output from a console 102*a* in an imaging room 601*a*, rejection or the like may occur. To prevent this, each of the plurality of radiation imaging apparatuses 101 is connected to a predetermined console 102 of the plurality of consoles 102. For example, radiation imaging apparatuses 101*aa* and 101*ab* are connected to the console 102a, and the radiation imaging apparatuses 101ba and 101bb are connected to a console 102b. At this time, for example, the radiation imaging apparatuses 101aa and 101ab do not comply with a detection signal representing that the start of radiation irradiation is detected, which is output from the radiation imaging apparatus 101ba or 101bb connected to the console 102b. Each radiation imaging apparatus 101 operates in accordance with only the connected console 102, thereby suppressing an influence from the other imaging room 601.

For example, when transmitting/receiving a signal between the radiation imaging apparatus 101 and the console 102 in the same imaging room 601, the radiation imaging apparatus 101 holds the ID of the console 102 and the ID of the radiation imaging apparatus 101 associated with the console 102 in the storage unit 214. A signal is generated such that the signal output from the console 102 to cause a state transition or the detection signal output from the radiation imaging apparatus 101 that has detected the start of radiation irradiation includes the ID of the console 102 that has issued the instruction or the ID of the radiation imaging apparatus 101. Upon receiving the signal, the radiation imaging apparatus 101 determines whether the console 102 or radiation imaging apparatus 101 of the transmission source matches the ID of the console 102 or the ID of the radiation imaging apparatus 101 registered in the storage unit 214. If the apparatus matches the information held in the storage unit 214, a response to the received signal is returned. If the pieces of information do not match, the sent signal is determined to be a signal transmitted from the other imaging room 601 and rejected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-006686, filed Jan. 18, 2018, which is hereby incorporated by reference wherein in its entirety.

What is claimed is:

1. A radiation imaging system including a plurality of radiation imaging apparatuses each configured to generate radiation image data corresponding to a dose of radiation emitted by a radiation generator,
   each of the plurality of radiation imaging apparatuses having
   an arrangement capable of detecting that radiation irradiation from the radiation generator is started, and comprising
   an output unit configured to output a first detection signal representing that the radiation imaging apparatus itself has detected a start of radiation irradiation, and a receiving unit configured to receive a second detection signal representing that another radiation imaging apparatus has detected the start of radiation irradiation,
   wherein in a case in which the start of radiation irradiation is detected in a first state capable of detecting the start of radiation irradiation, each of the plurality of radiation imaging apparatuses transitions to a second state for generating the radiation image data and causes the output unit to output the first detection signal,
   the radiation imaging apparatus that has transitioned to the second state in the plurality of radiation imaging apparatuses generates the radiation image data regardless of reception of the second detection signal by the receiving unit, and
   in a case in which the receiving unit has received the second detection signal, the radiation imaging apparatus in the first state in the plurality of radiation imaging apparatuses transitions to a third state in which power consumption is lower than that in the first state.

2. The system according to claim 1, wherein the radiation imaging apparatus that has detected the start of radiation irradiation in the plurality of radiation imaging apparatuses causes the output unit to output the first detection signal after an elapse of a predetermined time from the detection of the start of radiation irradiation.

3. The system according to claim 1, wherein the radiation imaging apparatus that has detected the start of radiation irradiation in the plurality of radiation imaging apparatuses causes the output unit to output the first detection signal after capturing of a radiation image ends, and the radiation image data is output.

4. The system according to claim 1, wherein the radiation imaging apparatus in the first state in the plurality of radiation imaging apparatuses
   transitions to the second state and causes the output unit to output the first detection signal in a case in which the start of radiation irradiation is detected during a time from the reception of the second detection signal by the receiving unit to an elapse of a predetermined time, and
   transitions to the third state in which the power consumption is lower than that in the first state in a case in which the start of radiation irradiation is not detected during the time from the reception of the second detection signal by the receiving unit to the elapse of the predetermined time.

5. The system according to claim 1, wherein a radiation imaging apparatus designated by an operation of a user in the plurality of radiation imaging apparatuses does not transition to the third state regardless of the reception of the second detection signal by the receiving unit.

6. The system according to claim 1, wherein each of the plurality of radiation imaging apparatuses comprises a communication unit including the output unit and the receiving unit, and
   in the third state, each of the plurality of radiation imaging apparatuses reduces at least one of a communication intensity and a communication frequency of the communication unit.

7. The system according to claim 1, wherein each of the plurality of radiation imaging apparatuses comprises an image capturing unit including a plurality of pixels each configured to convert the radiation into a charge signal, and a circuit unit configured to generate the radiation image data from the charge signal, and
   in the third state, each of the plurality of radiation imaging apparatuses stops power supply to the image capturing unit.

8. The system according to claim 1, further comprising a console configured to transmit/receive a signal between the radiation generator and the plurality of radiation imaging apparatuses,
   wherein the console transmits, to each of the plurality of radiation imaging apparatuses, a transition signal to make a transition to the first state,
   each of the plurality of radiation imaging apparatuses transitions to the first state in accordance with the transition signal, and
   after the transmission of the transition signal, the console transmits, to the radiation generator, a signal to start radiation irradiation.

9. The system according to claim 8, wherein each of the plurality of radiation imaging apparatuses receives, via the console, the second detection signal representing that the other radiation imaging apparatus has detected the start of radiation irradiation.

10. The system according to claim 8, wherein each of the plurality of radiation imaging apparatuses receives a detection signal, as the second detection signal without an intervention of the console, output from the other radiation imaging apparatus to represent that the start of radiation irradiation is detected.

11. The system according to claim 8, further comprising a plurality of consoles,
wherein each of the plurality of radiation imaging apparatuses
is connected to a predetermined console of the plurality of consoles, and
does not comply with a detection signal representing that the start of radiation irradiation is detected by a radiation imaging apparatus connected to a different console in the plurality of consoles.

12. The system according to claim 8, wherein each of the plurality of radiation imaging apparatuses and the console are connected by wireless communication.

13. The system according to claim 1, wherein each of the plurality of radiation imaging apparatuses includes a counter configured to count time from the transition to the first state to the detection of the start of radiation irradiation, and
the radiation imaging system compares count values of the counters between the plurality of radiation imaging apparatuses, thereby identifying the radiation imaging apparatus that has detected the start of radiation irradiation in the plurality of radiation imaging apparatuses.

14. A radiation imaging apparatus having an arrangement capable of generating radiation image data corresponding to a dose of radiation and detecting that radiation irradiation is started, comprising
an output unit configured to output a first detection signal representing that the radiation imaging apparatus itself has detected a start of radiation irradiation, and a receiving unit configured to receive a second detection signal representing that another radiation imaging apparatus has detected the start of radiation irradiation,
wherein in capturing a radiation image,
in a case in which the start of radiation irradiation is detected in a first state capable of detecting the start of radiation irradiation, the radiation imaging apparatus transitions to a second state for generating the radiation image data and causes the output unit to output the first detection signal,
the radiation imaging apparatus that has transitioned to the second state generates the radiation image data regardless of reception of the second detection signal by the receiving unit, and
in a case in which the receiving unit has received the second detection signal in the first state, the radiation imaging apparatus transitions to a third state in which power consumption is lower than that in the first state.

* * * * *